(12) United States Patent
Bohlin et al.

(10) Patent No.: US 10,548,882 B2
(45) Date of Patent: *Feb. 4, 2020

(54) CAMSYLATE SALT

(71) Applicant: AstraZeneca AB, Sodertalje (SE)

(72) Inventors: Martin Hans Bohlin, Cheshire (GB); Craig Robert Stewart, Cheshire (GB)

(73) Assignee: ASTRAZENECA AB, Sodertalje (SE)

( * ) Notice: Subject to any disclaimer, the term of this patent is extended or adjusted under 35 U.S.C. 154(b) by 69 days.

This patent is subject to a terminal disclaimer.

(21) Appl. No.: 13/916,754

(22) Filed: Jun. 13, 2013

(65) Prior Publication Data

US 2014/0031379 A1  Jan. 30, 2014

Related U.S. Application Data

(60) Provisional application No. 61/662,592, filed on Jun. 21, 2012.

(51) Int. Cl.
*A61K 31/4439* (2006.01)
*C07D 401/10* (2006.01)
*A61K 45/06* (2006.01)

(52) U.S. Cl.
CPC .......... *A61K 31/4439* (2013.01); *A61K 45/06* (2013.01); *C07D 401/10* (2013.01)

(58) Field of Classification Search
CPC ... A61K 31/4439; A61K 45/06; C07D 401/10
See application file for complete search history.

(56) References Cited

U.S. PATENT DOCUMENTS

| | | | |
|---|---|---|---|
| 8,415,483 B2 | 4/2013 | Csjernyik et al. | |
| 8,865,911 B2 | 10/2014 | Csjernyik et al. | |
| 9,000,182 B2 | 4/2015 | Karlstrom et al. | |
| 9,000,183 B2 | 4/2015 | Karlstrom et al. | |
| 9,000,184 B2 | 4/2015 | Karlstrom et al. | |
| 9,000,185 B2 | 4/2015 | Karlstrom et al. | |
| 9,248,129 B2 | 2/2016 | Csjernyik et al. | |
| 2004/0116478 A1* | 6/2004 | Moon | C07D 211/90 514/355 |
| 2011/0144154 A1* | 6/2011 | Fournet | C07D 215/10 514/311 |
| 2012/0165347 A1* | 6/2012 | Csjernyik et al. | 514/256 |
| 2013/0317014 A1 | 11/2013 | Dillard et al. | |
| 2013/0345246 A1 | 12/2013 | Karlstrom et al. | |
| 2013/0345247 A1 | 12/2013 | Karlstrom et al. | |
| 2013/0345248 A1 | 12/2013 | Karlstrom et al. | |
| 2013/0345272 A1 | 12/2013 | Karlstrom et al. | |
| 2014/0200223 A1 | 7/2014 | Cacatian et al. | |
| 2014/0288091 A1 | 9/2014 | Minidis et al. | |
| 2016/0184303 A1 | 6/2016 | Csjernyik et al. | |

FOREIGN PATENT DOCUMENTS

| | | |
|---|---|---|
| JP | 2009539983 A | 11/2009 |
| JP | 2010517963 | 5/2010 |
| JP | 2010526808 | 8/2010 |
| RU | 2401658 C2 | 10/2010 |
| WO | WO2002098462 | 12/2002 |
| WO | WO2005094822 | 10/2005 |
| WO | WO-2006065277 A2 | 6/2006 |
| WO | WO2006138264 | 12/2006 |
| WO | WO2007058601 | 5/2007 |
| WO | WO-2007058602 A2 | 5/2007 |
| WO | WO2007076247 | 7/2007 |
| WO | WO2007100536 | 9/2007 |
| WO | WO-2007146225 A2 | 12/2007 |
| WO | WO2008076043 | 6/2008 |
| WO | WO2009100169 | 8/2009 |
| WO | WO2010013794 | 2/2010 |
| WO | WO2010021680 | 2/2010 |
| WO | WO2010030954 | 3/2010 |
| WO | WO2010105179 | 9/2010 |
| WO | WO2011002407 | 1/2011 |
| WO | WO2011002408 | 1/2011 |
| WO | WO2011106414 | 9/2011 |
| WO | WO2011123674 | 10/2011 |
| WO | WO2011130741 | 10/2011 |
| WO | WO2012019056 | 2/2012 |
| WO | WO2012040641 | 3/2012 |
| WO | WO2012071458 | 5/2012 |
| WO | WO2012087237 | 6/2012 |

OTHER PUBLICATIONS

STN, pp. 9-13, obtained Feb. 3, 2015.*
Scifinder, pp. 2-5, obtained Feb. 3, 2015.*
Scifinder, p. 1, obtained Feb. 3, 2015.*
Kumar et al. "Effect of Counterions on Physicochemical Properties of Prazosin Salts" AAPS PharmSciTech, 2013, vol. 14(1), pp. 141-150.*
Evin et al., "BACE inhibitors as potential therapeutics for Alzheimer's disease," Recent Patents on CNS Drug Discovery, Bentham Science Publishers Ltd, NL, vol. 2, No. 3, Nov. 1, 2007 (Nov. 1, 2007), pp. 188-199.
Hong et al., "Structure of the Protease Domain of Memapsin 2 (β-Secretase) Complexed with Inhibitor," Science 2000, 290, 5489, pp. 150-153.
John et al, "Human β-Secretase (BACE) and BACE Inhibitors," Journal of Medicinal Chemistry, 2003, 46, pp. 4625-4630.
Roberds et al, "BACE knockout mice are healthy despite lacking the primary β-secretase activity in brain: implications for Alzheimer's disease therapeutics," Human Molecular Genetics, 2001, 10, pp. 1317-1324.

(Continued)

*Primary Examiner* — Yong S. Chong
(74) *Attorney, Agent, or Firm* — White & Case LLP

(57) ABSTRACT

A camsylate salt of (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine, pharmaceutical compositions containing the salt and therapeutic uses of the salt for treating Aβ-related pathologies such as Alzheimer's Disease, Down's syndrome, β-amyloid angiopathy and conditions such as dementia including dementia of mixed vascular and degenerative origin, pre-senile dementia, senile dementia and dementia associated with Parkinson's disease, progressive supranuclear palsy or cortical basal degeneration.

7 Claims, 1 Drawing Sheet

(56) References Cited

OTHER PUBLICATIONS

Sinha et al, "Purification and cloning of amyloid precursor protein β-secretase from human brain," Nature, 1999, 402, pp. 537-540.

Thompson et al., "Protein Conformational Misfolding and Amyloid Formation: Characteristics of a New Class of Disorders that Include Alzheimer's and Prion Diseases," Current Medicinal Chemistry, Oct. 2002, 9(19), pp. 1751-1762.

Berge et al., "Pharmaceutical Salts," Journal of Pharmaceutical Sciences, vol. 66, No. 1, pp. 1-19, Jan. 1977.

Bighley et al, "Salt Forms of Drugs and Absorption," Encyclopaedia of Pharmaceutical Technology, vol. 13. New York: Marcell-Decker, Inc. pp. 453-499, 1996.

Elder et al., "The Utility of Sulfonate Salts in Drug Development," Journal of Pharmaceutical Sciences, vol. 99, No. 7, pp. 2948-2961, Jul. 2010.

Gottfries et al., "Membrane Components Separate Early-Onset Alzheimer's Disease From Senile Dementia of the Alzheimer Type," International Psychogeriatrics, vol. 8, No. 3, pp. 365-372, 1996.

Makary et al., "Principles of salt formation," UK Journal of Pharmaceutical and Biosciences, vol. 2(4), 01-04, 2014.

Patel et al., "Pharmaceutical salts: a formulation trick or a clinical conundrum," The British Journal of Cardiology, vol. 16, No. 6, pp. 281-286, Nov./Dec. 2009.

Remenar et al., "Salt Selection and Simultaneous Polymorphism Assessment via High-Throughput Crystallization: The Case of Sertraline," Organic Process Research & Development 2003, 7, 990-996.

Rossor et al., "Neurochemical characteristics of early and late onset types of Alzheimer's disease," British Medical Journal, vol. 288, pp. 961-964, Mar. 31, 1984.

Stahl et al., Handbook of Pharmaceutical Salts Properties, Selection, and Use, Internatkional Union of Pure and Applied Chemistry (IUPAC), Second, Revised Edition, 2011, p. 336.

Carroll, https://endpts.com/mercks-leading-phiii-bace-drug-implodes-in-latest-alzheimers-disaster, accessed Apr. 19, 2017.

* cited by examiner

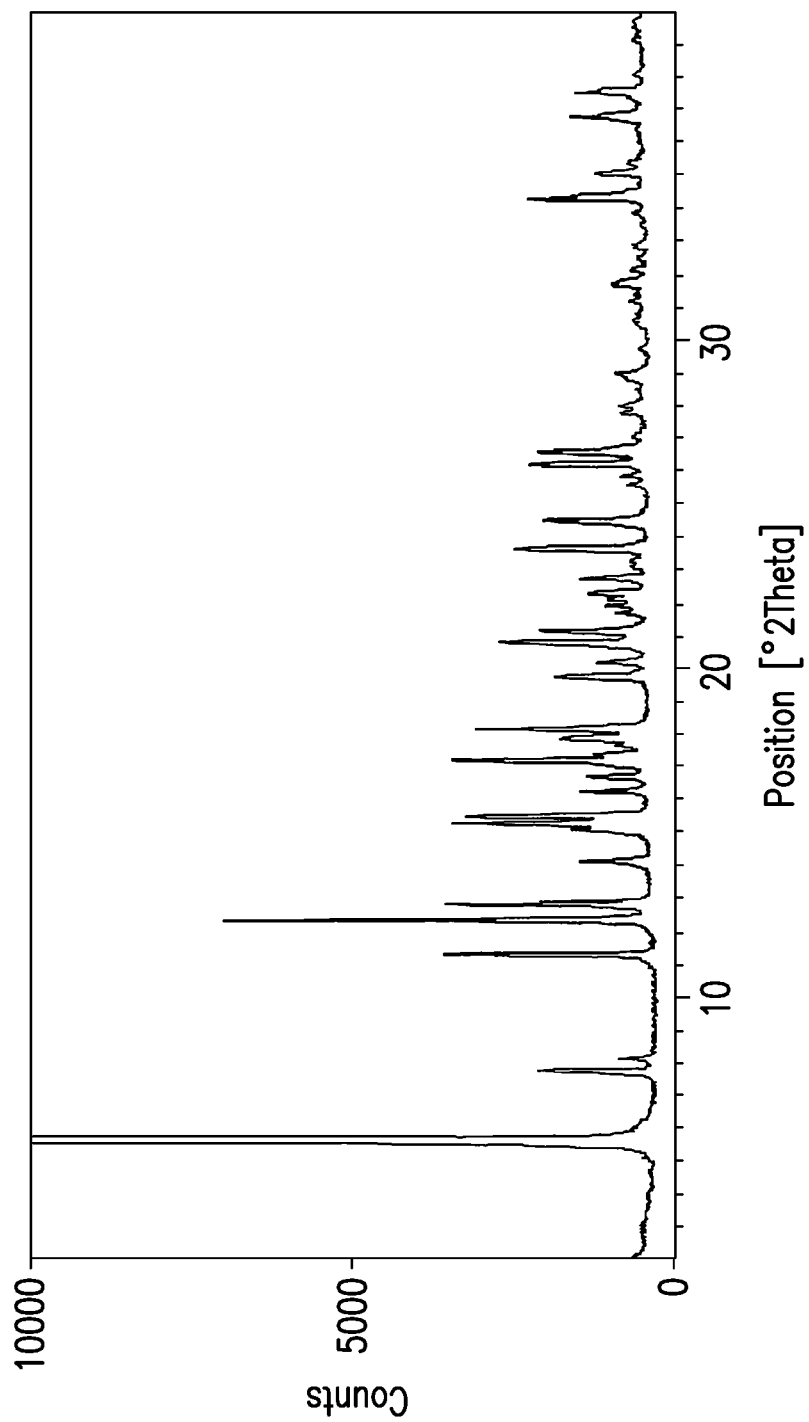

CAMSYLATE SALT

CROSS-REFERENCE TO RELATED APPLICATIONS

This application claims the benefit under 35 U.S.C. § 119(e) to U.S. Application No. 61/662,592 filed on Jun. 21, 2012, which is incorporated herein by reference.

TECHNICAL FIELD OF THE INVENTION

The present invention relates to a camphorsulfonic acid (camsylate) salt of (1r,1'R,4R)-4-methoxy-5''-methyl-6'-[5-(prop-1-yn-1-yl)pyridin-3-yl]-3'H-dispiro[cyclohexane-1, 2'-inden-1'2'-imidazole]-4''-amine, and to pharmaceutical compositions containing the salt. In addition, the present invention relates to therapeutic methods using the salt for the treatment and/or prevention of Aβ-related pathologies such as Down's syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer's Disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

BACKGROUND

The prime neuropathological event distinguishing Alzheimer's disease (AD) is deposition of the 40-42 residue amyloid β-peptide (Aβ) in brain parenchyma and cerebral vessels. A large body of genetic, biochemical and in vivo data support a pivotal role for Aβ in the pathological cascade that eventually leads to AD. Patients usually present early symptoms (commonly memory loss) in their sixth or seventh decades of life. The disease progresses with increasing dementia and elevated deposition of Aβ. In parallel, a hyperphosphorylated form of the microtubule-associated protein tau accumulates within neurons, leading to a plethora of deleterious effects on neuronal function. The prevailing working hypothesis regarding the temporal relationship between Aβ and tau pathologies states that Aβ deposition precedes tau aggregation in humans and animal models of the disease. Within this context, it is worth noting that the exact molecular nature of Aβ, mediating this pathological function is presently an issue under intense study. Most likely, there is a continuum of toxic species ranging from lower order Aβ oligomers to supramolecular assemblies such as Aβ fibrils.

The Aβ peptide is an integral fragment of the Type I protein APP (Aβ amyloid precursor protein), a protein ubiquitously expressed in human tissues. Since soluble Aβ can be found in both plasma and cerebrospinal fluid (CSF), and in the medium from cultured cells, APP has to undergo proteolysis. There are three main cleavages of APP that are relevant to the pathobiology of AD, the so-called α-, β-, and γ-cleavages. The α-cleavage, which occurs roughly in the middle of the Aβ domain in APP is executed by the metalloproteases ADAM10 or ADAM17 (the latter also known as TACE). The β-cleavage, occurring at the N terminus of Aβ, is generated by the transmembrane aspartyl protease Beta site APP Cleaving Enzyme1 (BACE1). The γ-cleavage, generating the Aβ C termini and subsequent release of the peptide, is effected by a multi-subunit aspartyl protease named γ-secretase. ADAM10/17 cleavage followed by γ-secretase cleavage results in the release of the soluble p3 peptide, an N-terminally truncated Aβ fragment that fails to form amyloid deposits in humans. This proteolytic route is commonly referred to as the non-amyloidogenic pathway. Consecutive cleavages by BACE1 and γ-secretase generates the intact Aβ peptide, hence this processing scheme has been termed the amyloidogenic pathway. With this knowledge at hand, it is possible to envision two possible avenues of lowering Aβ production: stimulating non-amyloidogenic processing, or inhibit or modulate amyloidogenic processing. This application focuses on the latter strategy, inhibition or modulation of amyloidogenic processing.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630). ß-amyloid deposits are predominately an aggregate of Aß peptide, which in turn is a product of the proteolysis of amyloid precursor protein (APP). More specifically, Aß peptide results from the cleavage of APP at the C-terminus by one or more γ-secretases, and at the N-terminus by ß-secretase enzyme (BACE), also known as aspartyl protease or Asp2 or Beta site APP Cleaving Enzyme (BACE), as part of the ß-amyloidogenic pathway.

BACE activity is correlated directly to the generation of Aß peptide from APP (Sinha, et al, Nature, 1999, 402, 537-540), and studies increasingly indicate that the inhibition of BACE inhibits the production of Aß peptide (Roberds, S. L., et al, Human Molecular Genetics, 2001, 10, 1317-1324). BACE is a membrane bound type 1 protein that is synthesized as a partially active proenzyme, and is abundantly expressed in brain tissue. It is thought to represent the major β-secretase activity, and is considered to be the rate-limiting step in the production of amyloid-β-peptide (Aβ).

Drugs that reduce or block BACE activity should therefore reduce Aβ levels and levels of fragments of Aβ in the brain, or elsewhere where Aβ or fragments thereof deposit, and thus slow the formation of amyloid plaques and the progression of AD or other maladies involving deposition of Aβ or fragments thereof. BACE is therefore an important candidate for the development of drugs as a treatment and/or prophylaxis of Aβ-related pathologies such as Down's syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer's Disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

It would therefore be useful to inhibit the deposition of Aβ and portions thereof by inhibiting BACE through inhibitors such as the compounds provided herein.

The therapeutic potential of inhibiting the deposition of Aβ has motivated many groups to isolate and characterize secretase enzymes and to identify their potential inhibitors.

BRIEF DESCRIPTION OF THE DRAWING

FIG. 1 is an X-ray powder diffractogram of a camsylate salt of (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine.

DETAILED DESCRIPTION OF THE INVENTION

The present invention relates to a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine. The camsylate salt of (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine can alternatively be described as a camphorsulfonic acid salt of (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine.

One embodiment of the present invention is a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine, characterized in providing an X-ray powder diffraction (XRPD) pattern, exhibiting substantially the following peaks with d-m spacing values as depicted in Table 1:

TABLE 1

Peaks identified on X-ray powder diffraction

| Corrected Angles | d-spacing (Å) | Relative intensity |
|---|---|---|
| 5.66 | 15.60 | vs |
| 7.72 | 11.44 | m |
| 8.11 | 10.89 | vw |
| 11.30 | 7.83 | m |
| 12.35 | 7.16 | s |
| 12.83 | 6.89 | m |
| 14.07 | 6.29 | w |
| 15.05 | 5.88 | w |
| 15.24 | 5.81 | m |
| 15.47 | 5.72 | m |
| 16.24 | 5.45 | w |
| 16.68 | 5.31 | w |
| 17.17 | 5.16 | m |
| 17.33 | 5.11 | w |
| 17.62 | 5.03 | vw |
| 17.84 | 4.97 | w |
| 18.13 | 4.89 | m |
| 19.71 | 4.50 | m |
| 20.18 | 4.40 | w |
| 20.77 | 4.27 | m |
| 21.12 | 4.20 | m |
| 21.67 | 4.10 | vw |
| 21.88 | 4.06 | vw |
| 22.09 | 4.02 | vw |
| 22.29 | 3.99 | w |
| 22.73 | 3.91 | w |
| 23.11 | 3.84 | vw |
| 23.63 | 3.76 | m |
| 24.50 | 3.63 | m |
| 26.18 | 3.40 | m |
| 26.54 | 3.36 | m |
| 27.72 | 3.22 | vw |
| 27.95 | 3.19 | vw |
| 28.80 | 3.10 | vw |
| 28.93 | 3.08 | vw |
| 29.71 | 3.00 | vw |
| 30.56 | 2.92 | vw |
| 31.14 | 2.87 | vw |
| 31.64 | 2.83 | vw |
| 31.74 | 2.82 | vw |

TABLE 1-continued

Peaks identified on X-ray powder diffraction

| Corrected Angles | d-spacing (Å) | Relative intensity |
|---|---|---|
| 32.11 | 2.79 | vw |
| 32.84 | 2.72 | vw |
| 33.86 | 2.65 | vw |
| 34.30 | 2.61 | m |
| 36.78 | 2.44 | m |
| 37.49 | 2.40 | w |
| 40.23 | 2.24 | vw |
| 40.93 | 2.20 | vw |
| 41.32 | 2.18 | vw |
| 42.43 | 2.13 | w |
| 44.54 | 2.03 | vw |
| 46.29 | 1.96 | vw |
| 48.32 | 1.88 | vw |

Another embodiment of the present invention is a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine, characterized in providing an X-ray powder diffraction pattern, exhibiting substantially the following very strong, strong and medium peaks with d-spacing values as depicted in Table 2:

TABLE 2

Peaks identified on X-ray powder diffraction

| Corrected Angles | d-spacing (Å) | Relative intensity |
|---|---|---|
| 5.66 | 15.60 | vs |
| 7.72 | 11.44 | m |
| 11.30 | 7.83 | m |
| 12.35 | 7.16 | s |
| 12.83 | 6.89 | m |
| 15.24 | 5.81 | m |
| 15.47 | 5.72 | m |
| 17.17 | 5.16 | m |
| 18.13 | 4.89 | m |
| 19.71 | 4.50 | m |
| 20.77 | 4.27 | m |
| 21.12 | 4.20 | m |
| 23.63 | 3.76 | m |
| 24.50 | 3.63 | m |
| 26.18 | 3.40 | m |
| 26.54 | 3.36 | m |
| 34.30 | 2.61 | m |
| 36.78 | 2.44 | m |

As used herein the term camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine also encompasses all solvates and co-crystals thereof.

Alternative salts of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine include the succinate-, the hydrochloric-, the phosphate-, the sulfate-, the fumarate- and the 1.5 naphtalenedisulfonate salt.

In a particular aspect of the invention, there is provided a pharmaceutical composition comprising as active ingredient a therapeutically effective amount of a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine, in association with pharmaceutically acceptable excipients, carriers or diluents.

In another aspect of the invention, there is provided a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine for use as a medicament.

In another aspect of the invention, there is provided use of a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine, as a medicament for treating or preventing an Aβ-related pathology.

In another aspect of the invention, there is provided use of a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine, as a medicament for treating or preventing an Aβ-related pathology, wherein said Aβ-related pathology is Down's syndrome, a β-amyloid angiopathy, cerebral amyloid angiopathy, hereditary cerebral hemorrhage, a disorder associated with cognitive impairment, MCI ("mild cognitive impairment"), Alzheimer's Disease, memory loss, attention deficit symptoms associated with Alzheimer's disease, neurodegeneration associated with Alzheimer's Disease, dementia of mixed vascular origin, dementia of degenerative origin, pre-senile dementia, senile dementia, dementia associated with Parkinson's disease, progressive supranuclear palsy or cortical basal degeneration.

In another aspect of the invention, there is provided use of a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine, as a medicament for treating or preventing Alzheimer's Disease.

In another aspect of the invention, there is provided use of a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine, in the manufacture of a medicament for treating or preventing an Aβ-related pathology.

In another aspect of the invention, there is provided use of a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine, in the manufacture of a medicament for treating or preventing an Aβ-related pathology, wherein said Aβ-related pathology is Down's syndrome, a β-amyloid angiopathy, cerebral amyloid angiopathy, hereditary cerebral hemorrhage, a disorder associated with cognitive impairment, MCI ("mild cognitive impairment"), Alzheimer's Disease, memory loss, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy or cortical basal degeneration.

In another aspect of the invention, there is provided use of a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine, in the manufacture of a medicament for treating or preventing Alzheimer's Disease.

In another aspect of the invention, there is provided a method of inhibiting activity of BACE comprising contacting said BACE with a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine.

In another aspect of the invention, there is provided a method of treating or preventing an Aβ-related pathology in a patient in need thereof, comprising administering to said patient a therapeutically effective amount of a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine.

In another aspect of the invention, there is provided a method of treating or preventing an Aβ-related pathology in a patient in need thereof, comprising administering to said patient a therapeutically effective amount of a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine, wherein said Aβ-related pathology is Down's syndrome, a β-amyloid angiopathy, cerebral amyloid angiopathy, hereditary cerebral hemorrhage, a disorder associated with cognitive impairment, MCI ("mild cognitive impairment"), Alzheimer's Disease, memory loss, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy or cortical basal degeneration.

In another aspect of the invention, there is provided a method of treating or preventing Alzheimer's Disease in a patient in need thereof, comprising administering to said patient a therapeutically effective amount of a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine.

In some embodiments, the present invention provides a method of inhibiting activity of BACE comprising contacting the BACE with a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine. BACE is thought to represent the major β-secretase activity, and is considered to be the rate-limiting step in the production of amyloid-β-protein (Aβ). Thus, inhibiting BACE through inhibitors such as the compounds provided herein would be useful to inhibit the deposition of Aβ and portions thereof. Because the deposition of Aβ and portions thereof is linked to diseases such Alzheimer's Disease, BACE is an important candidate for the development of drugs as a treatment and/or prophylaxis of Aβ-related pathologies such as Down's syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer's Disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

In some embodiments, the present invention provides a method for the prophylaxis of Aβ-related pathologies such as Down's syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer's Disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration comprising administering to a mammal (including human) a therapeutically effective amount of a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine.

In some embodiments, the present invention provides a method of treating or preventing Aβ-related pathologies such as Down's syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer's Disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration by administering to a mammal (including human) a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine and a cognitive and/or memory enhancing agent.

In some embodiments, the present invention provides a method of treating or preventing Aβ-related pathologies such as Down's syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer's Disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration by administering to a mammal (including human) a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine and a choline esterase inhibitor or anti-inflammatory agent.

In some embodiments, the present invention provides a method of treating or preventing Aβ-related pathologies such as Down's syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer's Disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration, or any other disease, disorder, or condition described herein, by administering to a mammal (including human) a compound of the present invention and an atypical antipsychotic agent. Atypical antipsychotic agents includes, but not limited to, Olanzapine (marketed as Zyprexa), Aripiprazole (marketed as Abilify), Risperidone (marketed as Risperdal), Quetiapine (marketed as Seroquel), Clozapine (marketed as Clozaril), Ziprasidone (marketed as Geodon) and Olanzapine/Fluoxetine (marketed as Symbyax).

In some embodiments, the mammal or human being treated with a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine has been diagnosed with a particular disease or disorder, such as those described herein. In these cases, the mammal or human being treated is in need of such treatment. Diagnosis, however, need not be previously performed.

The definitions set forth in this application are intended to clarify terms used throughout this application. The term "herein" means the entire application.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The anti-dementia treatment defined herein may be applied as a sole therapy or may involve, in addition to the compound of the invention, conventional chemotherapy. Such chemotherapy may include one or more of the following categories of agents: acetyl cholinesterase inhibitors, anti-inflammatory agents, cognitive and/or memory enhancing agents or atypical antipsychotic agents.

Such conjoint treatment may be achieved by way of the adjunct, concurrent, simultaneous, sequential or separate dosing of the individual components of the treatment. Such combination products employ the compounds of this invention.

Additional conventional chemotherapy may include one or more of the following categories of agents: (i) antidepressants, (ii) atypical antipsychotics, (iii) antipsychotics, (iv) anxiolytics, (v) anticonvulsants, (vi) currently used Alzheimer's therapies, (vii) Parkinson's therapies, (viii) migraine therapies, (ix) stroke therapies, (x) urinary incontinence therapies, (xi) neuropathic pain therapies, (xii) nociceptive pain therapies, (xiii) insomnia therapies and (xiv) mood stabilizers. Known treatments for the foregoing therapies may be employed in combination with the invention described herein.

Such combination products employ a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine within the dosage range described herein and the other pharmaceutically active compound or compounds within approved dosage ranges and/or as determined by a person skilled in the art.

Compounds of the present invention may be administered orally, parenteral, buccal, vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

An effective amount of a compound of the present invention for use in therapy of dementia is an amount sufficient to symptomatically relieve in a warm-blooded animal, particularly a human the symptoms of dementia, to slow the progression of dementia, or to reduce in patients with symptoms of dementia the risk of getting worse.

In addition to the compounds of the present invention, the pharmaceutical composition of this invention may also contain, or be co-administered (simultaneously or sequentially) with, one or more pharmacological agents of value in treating one or more disease conditions referred to herein.

The quantity of a camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine to be administered will vary for the patient being treated and will vary from about 10 ng/kg of body weight to 100 mg/kg of body weight per day and preferably will be from 10 ng/kg to 10 mg/kg per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

Methods of Preparation

Camsylate salt of (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine A camsylate salt of the compound (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine may be obtained by starting from a solution of (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine in a suitable solvent, for example 2-propanol, acetonitrile, or acetone or mixtures of these with water, followed by mixing the obtained solution with (1S)-(+)-10-camphorsulfonic acid directly or dissolved in a suitable solvent for example 2-propanol or water, at a temperature between room temperature and 80° C. Crystallization may be obtained by evaporation of solvent and/or by cooling the solution or directly as a salt reaction crystallization. Seed crystals may be used to start the crystallization. Seeds may be prepared from the batch itself by sampling a small volume of the solution and then rapidly cooling it to induce crystallization. Crystals are then added to the batch as seeds.

XRPD Analysis:

X-ray powder diffraction analysis (XRPD) was performed on samples prepared according to standard methods, for example those described in Giacovazzo, C. et al (1995), Fundamentals of Crystallography, Oxford University Press; Jenkins, R. and Snyder, R. L. (1996), Introduction to X-Ray Powder Diffractometry, John Wiley & Sons, New York; Bunn, C. W. (1948), Chemical Crystallography, Clarendon Press, London; or Klug, H. P. & Alexander, L. E. (1974), X-ray Diffraction Procedures, John Wiley and Sons, New York. X-ray diffraction analyses were performed using a PANanlytical X'Pert PRO MPD diffractometer for 96 minutes from 1 to 60° 2θ. XRPD distance values may vary in the range ±2 on the last decimal place.

The relative intensities are derived from diffractograms measured with variable slits.

The measured relative intensities vs. the strongest peak are given as very strong (vs) above 50%, as strong (s) between 25 and 50%, as medium (m) between 10 and 25%, as weak (w) between 5 and 10% and as very weak (vw) under 5% relative peak height. It will be appreciated by a person skilled in the art that the XRPD intensities may vary between different samples and different sample preparations for a variety of reasons including preferred orientation. It will also be appreciated by a person skilled in the art that smaller shifts in the measured Angle and hence the d-spacing may occur for a variety of reasons including variation of sample surface level in the diffractometer.

EXAMPLES

Example 1

6'-Bromospiro[cyclohexane-1,2'-indene]-1',4(3'H)-dione

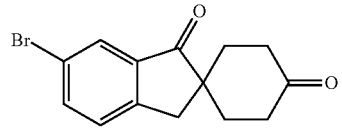

Potassium tert-butoxide (223 g, 1.99 mol) was charged to a 100 L reactor containing a stirred mixture of 6-bromo-1-indanone (8.38 kg, 39.7 mol) in THF (16.75 L) at 20-30° C. Methyl acrylate (2.33 L, 25.8 mol) was then charged to the mixture during 15 minutes keeping the temperature between 20-30° C. A solution of potassium tert-butoxide (89.1 g, 0.79 mol) dissolved in THF (400 mL) was added were after methyl acrylate (2.33 L, 25.8 mol) was added during 20 minutes at 20-30° C. A third portion of potassium tert-butoxide (90 g, 0.80 mol) dissolved in THF (400 mL) was then added, followed by a third addition of methyl acrylate (2.33 L, 25.8 mol) during 20 minutes at 20-30° C. Potassium tert-butoxide (4.86 kg, 43.3 mol) dissolved in THF (21.9 L) was charged to the reactor during 1 hour at 20-30° C. The reaction was heated to approximately 65° C. and 23 L of solvent was distilled off. Reaction temperature was lowered to 60° C. and 50% aqueous potassium hydroxide (2.42 L, 31.7 mol) dissolved in water (51.1 L) was added to the mixture during 30 minutes at 55-60° C. were after the mixture was stirred for 6 hours at 60° C., cooled to 20° C. during 2 hours. After stirring for 12 hours at 20° C. the solid material was filtered off, washed twice with a mixture of water (8.4 L) and THF (4.2 L) and then dried at 50° C. under vacuum to yield 6'-bromospiro[cyclohexane-1,2'-indene]-1',4(3'H)-dione (7.78 kg; 26.6 mol). $^1$H NMR (500 MHz, DMSO-$d_6$) δ ppm 1.78-1.84 (m, 2H), 1.95 (td, 2H), 2.32-2.38 (m, 2H), 2.51-2.59 (m, 2H), 3.27 (s, 2H), 7.60 (d, 1H), 7.81 (m, 1H), 7.89 (m, 1H).

Example 2

(1r,4r)-6'-Bromo-4-methoxyspiro[cyclohexane-1,2'-inden]-1'(3'H)-one

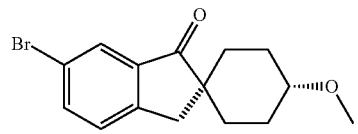

Borane tert-butylamine complex (845 g, 9.7 mol) dissolved in DCM (3.8 L) was charged to a slurry of 6'-Bromospiro[cyclohexane-1,2'-indene]-1',4(3'H)-dione (7.7 kg, 26.3 mol) in DCM (42.4 L) at approximately 0-5° C. over approximately 25 minutes. The reaction was left with stirring at 0-5° C. for 1 hour were after analysis confirmed that the conversion was >98%. A solution prepared from sodium chloride (2.77 kg), water (13.3 L) and 37% hydrochloric acid (2.61 L, 32 mol) was charged. The mixture was warmed to approximately 15° C. and the phases separated after settling into layers. The organic phase was returned to the reactor, together with methyl methanesulfonate (2.68 L, 31.6 mol) and tetrabutylammonium chloride (131 g, 0.47 mol) and the mixture was vigorously agitated at 20° C. 50% Sodium hydroxide (12.5 L, 236 mol) was then charged to the vigorously agitated reaction mixture over approximately 1 hour and the reaction was left with vigorously agitation overnight at 20° C. Water (19 L) was added and the aqueous phase discarded after separation. The organic layer was heated to approximately 40° C. and 33 L of solvent were distilled off. Ethanol (21 L) was charged and the distillation resumed with increasing temperature (22 L distilled off at up to 79° C.). Ethanol (13.9 L) was charged at approximately 75° C. Water (14.6 L) was charged over 30 minutes keeping the temperature between 72-75° C. Approximately 400 mL of the solution is withdrawn to a 500 mL polythene bottle and the sample crystallised spontaneously. The batch was cooled to 50° C. were the crystallised slurry sample was added back to the solution. The mixture was cooled to 40° C. The mixture was cooled to 20° C. during 4 hours were after it was stirred overnight. The solid was filtered off, washed with a mixture of ethanol (6.6 L) and water (5 L) and dried at 50° C. under vacuum to yield (1r,4r)-6'-bromo-4-methoxyspiro[cyclohexane-1,2'-inden]-1'(3'H)-one (5.83 kg, 18.9 mol) $^1$H NMR (500 MHz, DMSO-$d_6$) δ ppm 1.22-1.32 (m, 2H), 1.41-1.48 (m, 2H), 1.56 (td, 2H), 1.99-2.07 (m, 2H), 3.01 (s, 2H), 3.16-3.23 (m, 1H), 3.27 (s, 3H), 7.56 (d, 1H), 7.77 (d, 1H), 7.86 (dd, 1H).

Example 3

(1r,4r)-6'-Bromo-4-methoxyspiro[cyclohexane-1,2'-inden]-1'(3'H)-imine hydrochloride

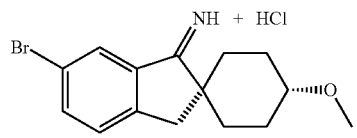

(1r,4r)-6'-Bromo-4-methoxyspiro[cyclohexane-1,2'-inden]-1'(3'H)-one (5.82 kg; 17.7 mol) was charged to a 100 L reactor at ambient temperature followed by titanium (IV)ethoxide (7.4 L; 35.4 mol) and a solution of tert-butylsulfinamide (2.94 kg; 23.0 mol) in 2-methyltetrahydrofuran (13.7 L). The mixture was stirred and heated to 82° C. After 30 minutes at 82° C. the temperature was increased further (up to 97° C.) and 8 L of solvent was distilled off. The reaction was cooled to 87° C. and 2-methyltetrahydrofuran (8.2 L) was added giving a reaction temperature of 82° C. The reaction was left with stirring at 82° C. overnight. The reaction temperature was raised (to 97° C.) and 8.5 L of solvent was distilled off. The reaction was cooled down to 87° C. and 2-methyltetrahydrofuran (8.2 L) was added giving a reaction temperature of 82° C. After 3.5 hours the reaction temperature was increased further (to 97° C.) and 8 L of solvent was distilled off. The reaction was cooled to 87° C. and 2-methyltetrahydrofuran (8.2 L) was added giving a reaction temperature of 82° C. After 2 hours the reaction temperature was increased further (to 97° C.) and 8.2 L of solvent was distilled off. The reaction was cooled to 87° C. and 2-methyltetrahydrofuran (8.2 L) was added giving a reaction temperature of 82° C. The reaction was stirred overnight at 82° C. The reaction temperature was increased further (to 97° C.) and 8 L of solvent was distilled off. The reaction was cooled down to 25° C. Dichloromethane (16.4 L) was charged. To a separate reactor water (30 L) was added and agitated vigorously and sodium sulfate (7.54 kg) was added and the resulting solution was cooled to 10° C. Sulfuric acid (2.3 L, 42.4 mol) was added to the water solution and the temperature was adjusted to 20° C. 6 L of the acidic water solution was withdrawn and saved for later. The organic reaction mixture was charged to the acidic water solution over 5 minutes with good agitation. The organic reaction vessel was washed with dichloromethane (16.4 L), and the dichloromethane wash solution was also added to the acidic water. The mixture was stirred for 15 minutes and then allowed to settle for 20 minutes. The lower aqueous phase was run off, and the saved 6 L of acidic wash was added followed by water (5.5 L). The mixture was stirred for 15 minutes and then allowed to settle for 20 minutes. The lower organic layer was run off to carboys and the upper water layer was discarded. The organic layer was charged back to the vessel followed by sodium sulfate (2.74 kg), and the mixture was agitated for 30 minutes. The sodium sulfate was filtered off and washed with dichloromethane (5.5 L) and the combined organic phases were charged to a clean vessel. The batch was heated for distillation (collected 31 L max temperature 57° C.). The batch was cooled to 40° C. and dichloromethane (16.4 L) was added. The batch was heated for distillation (collected 17 L max temperature 54° C.). The batch was cooled to 20° C. and dichloromethane (5.5 L) and ethanol (2.7 L) were. 2 M hydrogen chloride in diethyl ether (10.6 L; 21.2 mol) was charged to the reaction over 45 minutes keeping the temperature between 16-23° C. The resulting slurry was stirred at 20° C. for 1 hour whereafter the solid was filtered off and washed 3 times with a 1:1 mixture of dichloromethane and diethyl ether (3×5.5 L). The solid was dried at 50° C. under vacuum to yield (1r,4r)-6'-bromo-4-methoxyspiro[cyclohexane-1,2'-inden]-1'(3'H)-imine hydrochloride (6.0 kg; 14.3 mol; assay 82% w/w by $^1$H NMR) $^1$H NMR (500 MHz, DMSO-$d_6$) δ ppm 130 (m, 2H), 1.70 (d, 2H), 1.98 (m, 2H), 2.10 (m, 2H), 3.17 (s, 2H), 3.23 (m, 1H), 3.29 (s, 3H), 7.61 (d, 1H), 8.04 (dd, 1H), 8.75 (d, 1H), 12.90 (br s, 2H).

Example 4

(1r,4r)-6'-Bromo-4-methoxy-5"-methyl-3'H-dispiro[cyclohexane-1,2'-inden-1'2'-imidazole]-4"(3"H)-thione

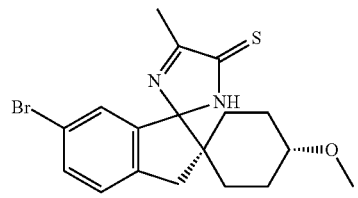

Trimethylorthoformate (4.95 L; 45.2 mol) and diisopropylethylamine (3.5 L; 20.0 mol) was charged to a reactor containing (1r,4r)-6'-bromo-4-methoxyspiro[cyclohexane-1, 2'-inden]-1'(3'H)-imine hydrochloride (6.25 kg; 14.9 mol) in isopropanol (50.5 L). The reaction mixture was stirred and heated to 75° C. during 1 hour so that a clear solution was obtained. The temperature was set to 70° C. and a 2 M solution of 2-oxopropanethioamide in isopropanol (19.5 kg; 40.6 mol) was charged over 1 hour, were after the reaction was stirred overnight at 69° C. The batch was seeded with (1r,4r)-6'-bromo-4-methoxy-5"-methyl-3'H-dispiro[cyclohexane-1,2'-inden-1'2'-imidazole]-4"(3"H)-thione (3 g; 7.6 mmol) and the temperature was lowered to 60° C. and stirred for 1 hour. The mixture was concentrated by distillation (distillation temperature approximately 60° C.; 31 L distilled off). Water (31 L) was added during 1 hour and 60° C. before the temperature was lowered to 25° C. during 90 minutes were after the mixture was stirred for 3 hours. The solid was filtered off, washed with isopropanol twice (2×5.2 L) and dried under vacuum at 40° C. to yield (1r,4r)-6'-bromo-4-methoxy-5"-methyl-3'H-dispiro[cyclohexane-1,2'-inden-1'2'-imidazole]-4"(3"H)-thione (4.87 kg; 10.8 mol; assay of 87% w/w by $^1$H NMR).

Example 5

(1r,1'R,4R)-6'-Bromo-4-methoxy-5"-methyl-3'H-dispiro[cyclohexane-1,2'-inden-1'2'-imidazole]-4"-amine D(+)-10-Camphorsulfonic acid salt

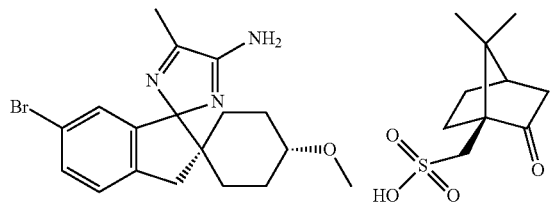

7 M Ammonia in methanol (32 L; 224 mol) was charged to a reactor containing (1r,4r)-6'-bromo-4-methoxy-5"-methyl-3'H-dispiro[cyclohexane-1,2'-inden-1'2'-imidazole]-4"(3"H)-thione (5.10 kg; 11.4 mol) and zinc acetate dihydrate (3.02 kg; 13.8 mol). The reactor was sealed and the mixture was heated to 80° C. and stirred for 24 hours, were after it was cooled to 30° C. 1-Butanol (51 L) was charged and the reaction mixture was concentrated by vacuum distilling off approximately 50 L. 1-Butanol (25 L) was added and the mixture was concentrated by vacuum distilling of 27 L. The mixture was cooled to 30° C. and 1 M sodium hydroxide (30 L; 30 mol) was charged. The biphasic mixture was agitated for 15 minutes. The lower aqueous phase was separated off. Water (20 L) was charged and the mixture was agitated for 30 minutes. The lower aqueous phase was separated off. The organic phase was heated to 70° C. were after (1S)-(+)-10-camphorsulfonic acid (2.4 kg; 10.3 mol) was charged. The mixture was stirred for 1 hour at 70° C. and then ramped down to 20° C. over 3 hours. The solid was filtered off, washed with ethanol (20 L) and dried in vacuum at 50° C. to yield (1r,4r)-6'-bromo-4-methoxy-5"-methyl-3'H-dispiro[cyclohexane-1,2'-inden-1'2'-imidazole]-4"-amine (+)-10-Camphor sulfonic acid salt (3.12 kg; 5.13 mol; assay 102% w/w by $^1$H NMR).

Example 6

(1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine Na$_2$PdCl$_4$ (1.4 g; 4.76 mmol) and 3-(di-tert-butylphosphonium)propane sulfonate (2.6 g; 9.69 mmol) dissolved in water (0.1 L) was charged to a vessel containing (1r,4r)-6'-bromo-4-methoxy-5"-methyl-3'H-dispiro[cyclohexane-1,2'-inden-1'2'-imidazole]-4"-amine (+)-10-camphorsulfonic acid salt (1 kg; 1.58 mol), potassium carbonate (0.763 kg; 5.52 mol) in a mixture of 1-butanol (7.7 L) and water (2.6 L). The mixture is carefully inerted with nitrogen whereafter 5-(prop-1-ynyl)pyridine-3-yl boronic acid (0.29 kg; 1.62 mol) is charged and the mixture is again carefully inerted with nitrogen. The reaction mixture is heated to 75° C. and stirred for 2 hours were after analysis showed full conversion. Temperature was adjusted to 45° C. Stirring was stopped and the lower aqueous phase was separated off. The organic layer was washed 3 times with water (3×4 L). The reaction temperature was adjusted to 22° C. and Phosphonics SPM32 scavenger (0.195 kg) was charged and the mixture was agitated overnight. The scavenger was filtered off and washed with 1-butanol (1 L). The reaction is concentrated by distillation under reduced pressure to 3 L. Butyl acetate (7.7 L) is charged and the mixture is again concentrated down to 3 L by distillation under reduced pressure. Butyl acetate (4.8 L) was charged and the mixture was heated to 60° C. The mixture was stirred for 1 hour were after it was concentrated down to approximately 4 L by distillation under reduced pressure. The temperature was set to 60° C. and heptanes (3.8 L) was added over 20 minutes. The mixture was cooled down to 20° C. over 3 hours and then left with stirring overnight. The solid was filtered off and washed twice with a 1:1 mixture of butyl acetate: heptane (2×2 L). The product was dried under vacuum at 50° C. to yield (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine (0.562 kg; 1.36 mol; assay 100% w/w by $^1$H NMR). $^1$H NMR (500 MHz, DMSO-d$_6$) δ ppm 0.97 (d, 1H), 1.12-1.30 (m, 2H), 1.37-1.51 (m, 3H), 1.83 (d, 2H), 2.09 (s, 3H), 2.17 (s, 2H), 2.89-3.12 (m, 3H), 3.20 (s, 3H), 6.54 (s, 2H), 6.83 (s, 1H), 7.40 (d, 1H), 7.54 (d, 1H), 7.90 (s, 1H). 8.51 (d, 1H), 8.67 (d, 1H)

Example 7

Preparation of Camsylate Salt of (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine 1.105 kg (1r,1'R,4R)-4-methoxy-5"-methyl-6'-[5-(prop-1-yn-1-yl)pyridin-3-yl]-3'H-dispiro[cyclohexane-1,2'-inden-1'2'-imidazole]-4"-amine was dissolved in 8.10 L 2-propanol and 475 mL water at 60° C. Then 1.0 mole equivalent (622 gram) (1S)-(+)-10 camphorsulfonic acid was charged at 60° C. The slurry was agitated until all (1S)-(+)-10 camphorsulfonic acid was dissolved. A second portion of 2-propanol was added (6.0 L) at 60° C. and then the contents were distilled until 4.3 L distillate was collected. Then 9.1 L Heptane was charged at 65° C. After a delay of one hour the batch became opaque. Then an additional distillation was performed at about 75° C. and 8.2 L distillate was collected. The batch was then cooled to 20° C. over 2 hrs and held at that temperature overnight. Then the batch was filtered and washed with a mixture of 1.8 L 2-propanol and 2.7 L heptane. Finally the substance was dried at reduced pressure and 50° C. The yield was 1.44 kg (83.6% w/w). $^1$H NMR (400 MHz, DMSO-d$_6$) δ ppm 12.12 (1H, s), 9.70 (2H, d, J 40.2), 8.81 (1H, d, J 2.1), 8.55 (1H, d, J 1.7), 8.05 (1H, dd, J 2.1, 1.7), 7.77 (1H, dd, J 7.8, 1.2), 7.50 (2H, m), 3.22 (3H, s), 3.19 (1H, d, J 16.1), 3.10 (1H, d, J 16.1), 3.02 (1H, m), 2.90 (1H, d, J 14.7), 2.60 (1H, m), 2.41 (1H, d, J 14.7), 2.40 (3H, s), 2.22 (1H, m), 2.10 (3H, s), 1.91 (3H, m), 1.81 (1H, m), 1.77 (1H, d, J 18.1), 1.50 (2H, m), 1.25 (6H, m), 0.98 (3H, s), 0.69 (3H, s).

BIOLOGICAL ASSAYS

The level of activity of the camsylate salt of (1r,1'R,4R)-4-methoxy-5''-methyl-6'-[5-(prop-1-yn-1-yl)pyridin-3-yl]-3'H-dispiro[cyclohexane-1,2'-inden-1'2''-imidazole]-4''-amine can be tested using the following methods:

TR-FRET Assay

The β-secretase enzyme used in the TR-FRET is prepared as follows:

The cDNA for the soluble part of the human β-Secretase (AA 1-AA 460) was cloned using the ASP2-Fc10-1-IRES-GFP-neoK mammalian expression vector. The gene was fused to the Fc domain of IgG1 (affinity tag) and stably cloned into HEK 293 cells. Purified sBACE-Fc was stored in −80° C. in 50 mM Glycine pH 2.5, adjusted to pH 7.4 with 1 M Tris and had a purity of 40%.

The enzyme (truncated form) was diluted to 6 μg/mL (stock 1.3 mg/mL) and TruPoint BACE1 Substrate to 200 nM (stock 120 μM) in reaction buffer (NaAcetate, chaps, triton x-100, EDTA pH4.5). Enzyme and compound in dimethylsulphoxide (final DMSO concentration 5%) was mixed and pre-incubated for 10 minutes at RT. Substrate was then added and the reaction was incubated for 15 minutes at RT. The reaction was stopped with the addition of 0.35 vol Stop solution (NaAcetate, pH 9). The fluorescence of the product was measured on a Victor II plate reader with excitation wavelengths of 340-485 nm and emission wavelengths of 590-615 nm. The final concentration of the enzyme was 2.7 μg/ml; the final concentration of substrate was 100 nM (Km of ~250 nM). The dimethylsulphoxide control, instead of test compound, defined the 100% activity level and 0% activity was defined by wells lacking enzyme (replaced with reaction buffer) or by a saturating dose of a known inhibitor, 2-amino-6-[3-(3-methoxyphenyl)phenyl]-3,6-dimethyl-5H-pyrimidin-4-one. A control inhibitor was also used in dose response assays and had an IC50 of ~150 nM.

The camsylate salt of (1r,1'R,4R)-4-methoxy-5''-methyl-6'-[5-(prop-1-yn-1-yl)pyridin-3-yl]-3'H-dispiro[cyclohexane-1,2'-inden-1'2''-imidazole]-4''-amine had an average IC$_{50}$ of 0.2 nM in this assay.

sAPPβ Release Assay

SH-SY5Y cells are cultured in DMEM/F-12 with Glutamax, 10% FCS and 1% non-essential amino acids and cryopreserved and stored at −140° C. at a concentration of 7.5-9.5×10$^6$ cells per vial. Cells are thawed and seeded at a conc. of around 10000 cells/well in DMEM/F-12 with Glutamax, 10% FCS and 1% non-essential amino acids to a 384-well tissue culture treated plate, 100 μL cell susp/well. The cell plates are then incubated for 7-24 h at 37° C., 5% CO$_2$. The cell medium is removed, followed by addition of 30 μL compound diluted in DMEM/F-12 with Glutamax, 10% FCS, 1% non-essential amino acids and 1% PeSt to a final conc. of 1% DMSO. The compounds are incubated with the cells for 17 h (overnight) at 37° C., 5% CO$_2$. Meso Scale Discovery (MSD) plates are used for the detection of sAPPβ release. MSD sAPPβ plates are blocked in 1% BSA in Tris wash buffer (40 μL/well) for 1 h on shake at r.t. and washed 1 time in Tris wash buffer (40 μL/well). 20 μL of medium is transferred to the pre-blocked and washed MSD sAPPβ microplates, and the cell plates are further used in an ATP assay to measure cytotoxicity. The MSD plates are incubated with shaking at r.t. for 2 h and the media discarded. 10 μL detection antibody is added (1 nM) per well followed by incubation with shaking at r.t. for 2 h and then discarded. 40 μL Read Buffer is added per well and the plates are read in a SECTOR Imager.

ATP Assay

As indicated in the sAPPβ release assay, after transferring 20 μL medium from the cell plates for sAPPβ detection, the plates are used to analyse cytotoxicity using a ViaLight™ Plus cell proliferation/cytotoxicity kit from Cambrex Bio-Science that measures total cellular ATP. The assay is performed according to the manufacture's protocol. Briefly, 10 μL cell lysis reagent is added per well. The plates are incubated at r.t. for 10 min. Two min after addition of 25 μL reconstituted ViaLight™ Plus ATP reagent, luminescence is measured. Tox threshold is a signal below 75% of the control.

The invention claimed is:

1. A camsylate salt of (1r,1'R,4R)-4-methoxy-5''-methyl-6'-[5-(prop-1-yn-1-yl)pyridin-3-yl]-3'H-dispiro[cyclohexane-1,2'-indene-1',2''-imidazol]-4''-amine:

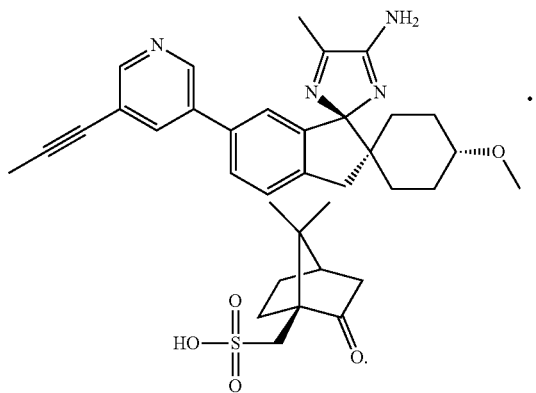

2. A crystalline camsylate salt of (1r,1'R,4R)-4-methoxy-5''-methyl-6'-[5-(prop-1-yn-1-yl)pyridin-3-yl]-3'H-dispiro[cyclohexane-1,2'-indene-1',2''-imidazol]-4''-amine:

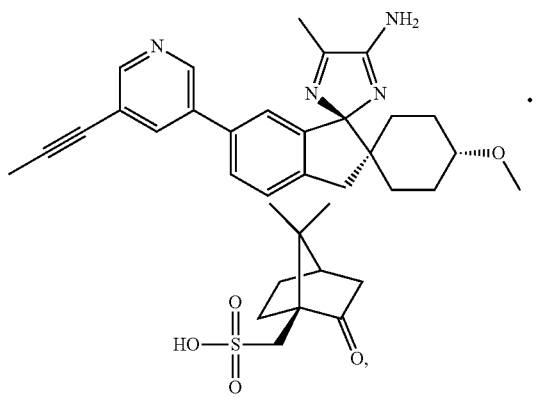

characterized in that said crystalline camsylate salt has an X-ray powder diffraction (XRPD) pattern, exhibiting substantially the following very strong, strong and medium peaks with d-values:

| Corrected Angles | d-spacing (Å) | Relative intensity |
|---|---|---|
| 5.66 | 15.60 | vs |
| 7.72 | 11.44 | m |
| 11.30 | 7.83 | m |
| 12.35 | 7.16 | s |
| 12.83 | 6.89 | m |
| 15.24 | 5.81 | m |
| 15.47 | 5.72 | m |
| 17.17 | 5.16 | m |
| 18.13 | 4.89 | m |
| 19.71 | 4.50 | m |
| 20.77 | 4.27 | m |
| 21.12 | 4.20 | m |
| 23.63 | 3.76 | m |
| 24.50 | 3.63 | m |
| 26.18 | 3.40 | m |
| 26.54 | 3.36 | m |
| 34.30 | 2.61 | m |
| 36.78 | 2.44 | m. |

3. A crystalline camsylate salt of (1r,1'R,4R)-4-methoxy-5''-methyl-6'-[5-(prop-1-yn-1-yl)pyridin-3-yl]-3'H-dispiro[cyclohexane-1,2'-indene-1',2''-imidazol]-4''-amine:

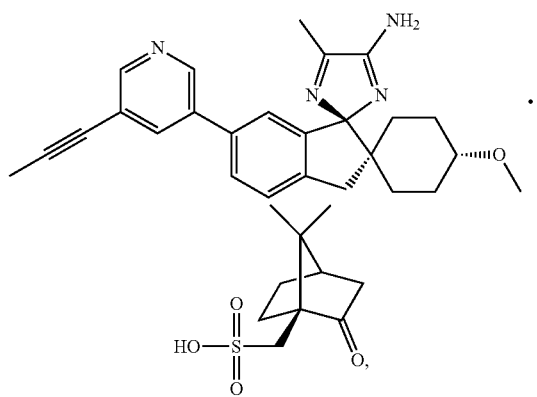

characterized in that said crystalline camsylate salt has an X-ray powder diffraction pattern essentially as shown in FIG. 1.

4. A pharmaceutical composition comprising as active ingredient a therapeutically effective amount of a salt according to claim 1, in association with at least one pharmaceutically acceptable excipient, carrier or diluent.

5. A method of treating an Aβ-related pathology in a patient in need thereof, comprising administering to said patient a therapeutically effective amount of a salt according to claim 1, wherein said Aβ-related pathology is Down's syndrome, a β-amyloid angiopathy, cerebral amyloid angiopathy, MCI ("mild cognitive impairment"), Alzheimer's Disease, neurodegeneration associated with Alzheimer's disease, dementia of degenerative origin, pre-senile dementia, senile dementia, dementia associated with Parkinson's disease, or cortical basal degeneration.

6. A method of treating Alzheimer's Disease in a patient in need thereof, comprising administering to said patient a therapeutically effective amount of a salt according to claim 1.

7. A crystalline camsylate salt of (1r,1'R,4R)-4-methoxy-5''-methyl-6'-[5-(prop-1-yn-1-yl)pyridin-3-yl]-3'H-dispiro[cyclohexane-1,2'-indene-1',2''-imidazol]-4''-amine:

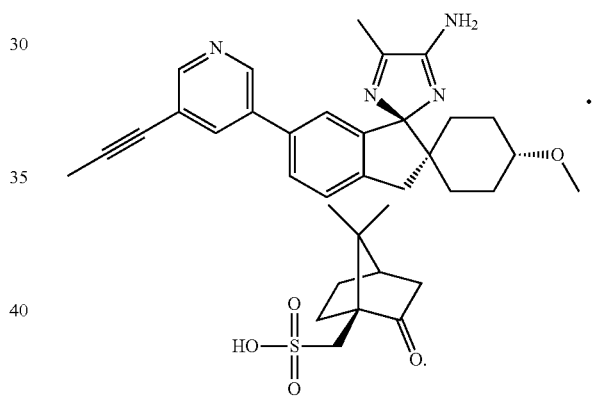

* * * * *